United States Patent [19]

Benzie et al.

[11] 4,096,171

[45] Jun. 20, 1978

[54] PROCESS FOR THE MANUFACTURE OF DICYANOBUTENE FROM BUTADIENE, HYDROGEN CYANIDE AND OXYGEN

[75] Inventors: Robert John Benzie; Dhafir Yusuf Waddan, both of Wilton, England

[73] Assignee: Imperial Chemical Industries Limited, London, England

[21] Appl. No.: 789,186

[22] Filed: Apr. 20, 1977

[30] Foreign Application Priority Data

Apr. 29, 1976 United Kingdom ............... 17493/76

[51] Int. Cl.$^2$ ........................................... C07C 120/02
[52] U.S. Cl. .................................................. 260/465.3
[58] Field of Search ...................................... 260/465.3

[56] References Cited

U.S. PATENT DOCUMENTS

| | | | |
|---|---|---|---|
| 3,553,246 | 1/1971 | Kominami et al. ................ | 260/465.3 |
| 3,709,921 | 1/1973 | Baird, Jr. et al. ................. | 260/465.3 |
| 3,849,472 | 11/1974 | Waddan ............................. | 260/465.3 |
| 3,869,501 | 3/1975 | Waddan ............................. | 260/465.3 |

FOREIGN PATENT DOCUMENTS 1,084,599  9/1967  United Kingdom.

*Primary Examiner*—Joseph Paul Brust
*Attorney, Agent, or Firm*—Cushman, Darby & Cushman

[57] ABSTRACT

Butadiene is converted directly to dicyanobutene by reacting with hydrogen cyanide and oxygen or an oxygen-containing gas in the presence of a catalyst comprising copper ions, chloride and/or bromide ions, and iodide ions, and of a solvent for the catalyst.

11 Claims, No Drawings

PROCESS FOR THE MANUFACTURE OF DICYANOBUTENE FROM BUTADIENE, HYDROGEN CYANIDE AND OXYGEN

This invention relates to organic nitriles, more specifically to dicyanobutene and to a method for its manufacture from butadiene.

It has already been proposed to manufacture dicyanobutene from butadiene by a two-stage process in which butadiene is chlorinated to give dichlorobutene, and the dichlorobutene is then reacted with hydrogen cyanide or an alkali metal cyanide to give dicyanobutene. Apart from the fact that two stages are involved, the method involves the introduction of chlorine and its subsequent removal. It has also been proposed to react butadiene with hydrogen cyanide in presence of a catalyst, for example a zerovalent nickel catalyst, as described, for example, in British Patent Specification No. 1,104,140, but commercially known methods introduce only one cyano group to give a mixture of pentenenitriles and methyl-butenenitriles. The pentenenitriles may subsequently be reacted with further hydrogen cyanide in a separate stage to give adiponitrile, but the latter compound cannot be obtained by this method from butadiene in a single stage in significant yield.

It has also, however, been proposed in U.S. Pat. Application Ser. No. 721,507, now U.S. Pat. No. 4,048,216, issued Sept. 13, 1977, to manufacture dicyanobutene directly from butadiene by reaction it with hydrogen cyanide and oxygen or an oxygen-containing gas in the presence of a catalyst comprising copper ions and halide ions and of a solvent for the catalyst.

We have now found that in the latter reaction the catalyst activity is enhanced and the reaction proceeds at a faster rate if there is used as the halide ions in the catalyst a mixture of chloride and/or bromide ions with iodide ions.

Our invention provides a process for the manufacture of dicyanobutene which comprises reacting butadiene with hydrogen cyanide and oxygen or an oxygen-containing gas mixture in the presence of a catalyst comprising copper ions, chloride and/or bromide ions, and iodide ions, and of a solvent for the catalyst.

The copper ions in the catalyst used in the process of our invention may be added in the cuprous or cupric form. Under the influence of the oxygen used in the process cuprous ions tend to be oxidised to cupric, whereas the hydrocyanation reaction tends to cause the cupric ions to be reduced to cuprous. The copper may be added to the raaction mixtured as a halide, for example as cuprous or cupric chloride, bromide or iodide (or as any mixture thereof). This may ensure the presence of chloride and/or bromide ion and of iodide ion, which are necessary constitutents of the catalyst, but it is not essential that the said ions be added in this way. Other copper salts may be used, especially the salts of organic acids, more especially the salts of aliphatic carboxylic acids and particularly the salts of alkane carboxylic acids having from 2 to 6 carbon atoms. As examples of such copper salts therre may be mentioned copper formate, acetate, propionate, butyrate, lactate, glycollate, acetylacetonate naphthenate, stearate and benzoate. Moreover, other sources of chloroide and/or bromide ion and of iodide ion may be used for example alkali metal and ammonium chloride, bromide and iodide as well as hydrogen chloride, bromide and iodide and chlorine, bromine and iodine themselves. Further, organic chlorine, bromine and iodine compounds may be used as the halide source, for example tetrabromoethane, chloracetic acid, bromoacetic acid, acetylbromide, dichlorobutene and dibromobutene, as well as hydrochlorides, hydrobromides and hydroiodides of organic bases and quaternary ammonium bromides and iodides. It is advantageous also for there to be present an alkali metal salt, for example a sodium, potassium or especially a lithium salt, or an alkaline earth metal salt, for example a beryllium, magnesium, calcium or barium salt. Such a salt is preferably a chloride, bromide or iodide, but may be, for example, an organic acid salt, especially a salt with one of the organic acids specified above as forming suitably copper salts. As examples of such salts there may be mentioned, lithium chloride, lithium bromide, lithium iodide, lithium acetate, lithium propionate, sodium bromide, sodium iodide, sodium acetate, potassium bromide, potassium iodide, potassium acetate and magnesium bromide.

Mixtures of bromide with iodide ion in the catalyst are particularly suitable. The uptake of oxygen may be assisted by the presence of oxygen carriers, for example, maganese compounds, e.g. manganese gluconate.

As solvents for the catalyst there may be used a wide variety of compounds. The basic requirements are that the catalyst components shall dissolve to a greater or less extent in the solvent and that the solvent shall not interfere with the reaction and shall not itself be extensively changed by the reaction. Thus olefinically unsaturated compounds which react with hydrogen cyanide under the reaction conditions are unsuitable, as are solvents, for example mercaptans, which would be oxidised by the oxygen-containing gas under the reaction conditions. The solvent should preferably be liquid at the reaction temperature and pressure. However, compounds which are normally solid under the reaction conditions may be used dissolved in another solvent.

Water is a suitable solvent a are many organic compounds. Particularly suitable classes or organic compounds include nitriles, alcohols, phenols, ethers, acids, ketones and amides. Suitable nitriles include aliphatic, cycloaliphatic, araliphatic and aromatic nitriles. More especially they include alkyl nitriles and alkylene dinitriles, particularly those having from 1 to 6 carbon atoms in the alkyl or alkylene residue, for example acetonitrile, propionitrile, butyronitrile, hexanonitrile, glutarodinitrile adiponitrile, dicyanobutene and succindinitrile, alkenyl nitriles, for example acrylonitrile, methacrylonitrile, butenenitriles, methyl butenenitriles and pentenenitriles, higher polynitriles, for example tetracyanoethylene, cycloalkyl nitriles, for example cyclohexyl cyanide, aralkyl nitriles, for example benzyl cyanide and $\alpha, \alpha'$-xylene dinitrile and aryl nitriles, for example benzonitriles, tolunitriles, phthalodinitrile and terephthalodinitrile. Particularly suitable nitriles include acetonitrile, propionitrile and adiponitrile.

Suitable alcohols include aliphatic, cycloaliphatic and araliphatic alcohols. More especially they include alkanols, particularly those having from 1 to 6 carbon atoms, for example methanol, ethanol, n-propanol, isopropanol, butanols, pentanols and hexanols, alkandiols, particularly those having from 1 to 6 carbon atoms, for example ethylene glycol, propane-1,2-diol, propane-1,3-diol, butane-1,4-diol, pentene-diols and hexanediols, alkane-polyols, for example glycerol and trimethylolpropane, aralkanols, for example benzyl alcohol and 2-phenylethanol, and cycloalkanols, for example cyclopentanol, methylcyclopentanols, cyclohexanol and methylcyclohexanols. Particularly suitable alcohols include ethanol and isopropanol.

Suitable phenols include phenol itself, alkylphenols, for example cresols, ethylphenols and xylenols, and halogenophenols, especially chlorophenols and di- and tri- chlorophenols. m-Cresol is a particularly suitable phenol.

Suitable ethers include aliphatic ethers araliphatic ethers, aromatic ethers and cyclic ethers. More especially they include dialkyl ethers, for example di-isopropyl ether and methyl butyl ether, bis-ethers and polyethers for example 1,2-dimethoxyethane, 1,2-dimethyoxypropane and diethyleneglycol dimethyl ether (diglyme), cyclic ethers, for example tetrahydrofuran, tetrahydropyran, dioxan, diphenylene oxide and crown ether (6, 7, 9, 10, 17, 18, 20, 21 -octahydrodibenzo (b, k) (1, 4, 7, 10, 13, 16) -hexaoxacyclooctadecene), alkyl aryl ethers, for example anisole and phenetole, diaralkyl ethers, for example dibenzyl ether, and diaryl ethers for example diphenyl oxide. Dimethyoxyethane, diglyme and tetrahydrofuran are particularly suitable ethers.

Suitable organic acids are especially the carboxylic acids. Suitable carboxylic acids include aliphatic, cycloaliphatic, araliphatic and aromatic carboxylic acids. More especially they include alkane carboxylic acids, particularly those having from 2 to 6 carbon atoms in the alkane residue, for example acetic acid, propionic acid, butyric acid, isobutyric acid, valeric acid or caproic acid, cycloalkane carboxylic acids, for example cyclohexane carboxylic acid and cyclohexylacetic acid, aralkyl carboxylic acids, for example phenylacetic acid, aryl carboxylic acids, for example benzoic acid, toluic acids and anisic acids, and napthenic acids. Acetic acid is particularly suitable.

Suitable ketones include aliphatic, cycloaliphatic, araliphatic, aromatic and cyclic ketones. More especially they include dialkyl ketones, particularly those having from 1 to 6 carbon atoms in the alkyl residues, for example acetone, methyl ethyl ketone and methyl isobutyl ketone, diketones, for example acetylacetone, cyclic ketones, for example cyclopentanone, methylcyclopentanone, cyclohexanone and methylcyclohexanone, alkyl aryl ketones, for example acetophenone, and diaryl ketones, for example benzophenone. Acetone and acetylacetone are particularly suitable ketones.

Suitable amides include in particular aliphatic carboxylic amides and their N-subsitituted derivatives. More especially they include alkane carboxylic amides, particularly those having from 1 to 4 carbon atoms, and their N-alkyl and N,N-dialkyl derivatives especially those having from 1 to 4 carbon atoms in the alkyl residues, for example formamide, N-methylformamide, N,N-dimethylformamide, acetamide, N,N-dimethylacetamide and propionamide. They also include cyclic amides for example N-methyl-2-pyrrolidone. Dimethylformamide is a particularly suitable amide.

Suitable solvents also include compounds which contain two or more of the functional groups which characterise, respectively, the said nitriles, alcohols, phenols, ethers, acids, ketones and amides, or contain one or more of the said functional groups in combination with some other group. Such compounds include, for example, ether-alcohols, for example ethylene glycol monomethyl and monoethyl ether, nitrile-acids, for example cyanoacetic acid and α-cyanovaleric acid, halogeno-acids, for example chloroacetic acid, dichloroacetic acid and trichloroacetic acid, and nitrile-estes, for example ethyl cyanoacetate.

Other suitable solvents include esters, especially the esters formed from the alcohols and acids already described as suitable solvents. Particularly suitable esters are the lower alkylesters (e.g. where lower alkyl has from 1 to 4 carbon atoms) of aliphatic mono- or di-carboxylic acids especially those having from 1 to 6 carbon atoms, for example methyl acetate, ethyl acetate, isopropyl acetate, ethyl propionate, methyl butyrate, dimethyl succinate, dimethyl glutarate and diethyl adipate.

Other suitable solvents include hydrocarbons and halogenated hydrocarbons. Such solvents include both aliphatic, cycloaliphatic and aromatic hydrocarbons, and their halogenated derivatives, for example hexane, cyclohexane, benzene, toluene, xylene, chloroform, carbon tetrachloride, trichloroethylene, tetrachlorethane, dibromoethane, chlorobenzene, bromobenzene, dichlorobenzene, trichlorobenzene and diphenyl.

Other suitable solvents include thioethers, that is sulphides, including cyclic sulphides, for example dimethyl sulphide, diethyl sulphide, dipropyl sulphide, dibutyl sulphide, diamyl sulphide, dihexyl sulphide, methyl ethyl sulphide, thiophen, tetrahydrothiophen, pentamethylene sulphide, dicyclohexyl sulphide, dibenzyl sulphide, diphenyl sulphide, ditolyl sulphide and thiodiglycol.

Other suitable solvents include sulphoxides and sulphones, especially dialkyl sulphoxides and sulphones, particularly where the alkyl group has from 1 to 6 carbon atoms, and cyclic sulphoxides and sulphones, for example dimethyl sulphoxide, diethyl sulphoxide, diethyl sulphone, dimethyl sulphone, tetramethylene sulphoxide, tetramethylene sulphone (sulpholane) and pentamethylene sulphoxide and pentamethylene sulphone.

The solvents may be used singly or in admixture with each other in any convenient proportions. Moreover the solvents may be used in admixture with other organic compounds which are not in themselves solvents for the catalyst.

The oxygen may be used as such or in admixture with non-reactive gases such as nitrogen. Air is a particularly suitable oxygen-containing gas, but mixtures of oxygen and nitrogen with a higher or lower proportion of oxygen than that of the air may also be used.

The reaction is conveniently carried out at temperatures within the range 10° to 150° C, preferably from 35° to 110° C. The reaction may be carried out at atmospheric pressure or at pressures above or below that of the atmosphere. The process may advantageously be operated under pressure, and pressures may, for example, be up to about 50 bar. Pressures in the range 2 to 10 bar absolute are very suitable.

The reaction may conveniently be carried out by passing butadiene and hydrogen cyanide in vapour form together with oxygen or an oxygen-contaning gas through a liquid comprising the catalyst and solvent under the selected temperature and pressure conditions. Alternatively, the butadiene and hydrogen cyanide may be kept in the liquid phase under pressure with the catalyst and solvent, and the oxygen or oxygen-containing gas passed through. It is not essential, however, for the oxygen or oxygen-containing gas to be contacted simultaneously with the catalyst and solvent. It is possible, for example, to pass butadiene and hydrogen cyanide on the one hand and oxygen-containing gas on the other hand alternately through the liquid comprising the catalyst and solvent. Passage of oxygen or oxygen-containing gas in these circumstances leads to a change in the colour of the liquid to dark brown.

The butadiene used in the process of our invention may contain other constitutents. For example the butadiene may be admixed with other $C_4$ hydrocarbons, for example butenes and butane. Instead of using butadiene itself, a crude $C_4$ stream from a cracker containng possibly less than 50% of butadiene may be used as the feed in our process to produce dicyabobutene.

Water is formed in the process of our invention, and it may be desirable, for example when using organic solvents, to remove the water from the reaction system. The water is usually taken up into the reactant gas stream and is preferably condensed out from the effluent gas stream at least in part, prior to any recycle.

In carrying out the process of our invention the molar ratio of hydrogen cyanide to butadiene may vary widely, for example over the range 1:10 to 10:1, but preferably over the range 1:2 to 4:1. The oxygen is preferably used in molar excess in relation to whichever of the hydrogen cyanide and butadiene is used in the smaller molar amount.

The catalyst is used in catalytic amount. The amount of copper ion may vary, for example, from 0.001 mole to 0.2 mole per mole of butadiene, although higher proportions are not excluded. The amount of chloride and/or bromide ion and iodide ion in total may vary, for example, within the same molar range, although we prefer that there is at least one mole of total said halide ion per mole of copper ion. The relative proportions of iodide to chloride and/or bromide may vary within wide limits, for example the iodide may vary from 0.1% to 90% of the combined chloride, bromide and iodide on a molar basis, but we prefer the iodide proportion to be between 1% and 10%. The amount of solvent used may vary widely. There should preferably be at least 1 mole of solvent per mole of copper ion, and amounts between 5 moles and 100 moles are convenient. When an alkali metal or alkaline earth metal compound is present it may be used in amounts up to several times the molar amount of copper, for example in amounts of from 0.5 to 15 moles per mole of copper.

The dicyanobutene obtained as the product of our process is normally present in the liquid reaction mixture and may be separated therefrom by conventional methods, for example by fractional distillation under reduced pressure, by extraction with solvents, or by a combination of such methods.

The process of our invention is particularly adapted to continuous operation. It may be convenient to take the reaction to only partial completion, to separate at least some of the product and to recycle unchanged material. For this reason times of contact with the catalyst may vary widely. Such times may vary from a few minutes, for example 5 minutes, up to many hours, for examle 50 hours.

The dicyanobutene product of our process is principally 1,4-dicyanobutene. This is a valuable intermediate, since it may, by hydrogenation of the double bond, be converted to adiponitrile which itself, on hydrogenation of the nitrile groups, give hexamethylene diamine, an intermediate useful in the manufacture of polymers, for example polyurethanes and especially polyamides, in particular polyamides made by polycondensation with dicarboxylic acids, for example with adipic acid to give polyhexamethylene adipamide (nylon 6.6) useful for the manufacture of mouldings and for melt-spinning into synthetic fibres.

The invention is illustrated but not limited by the following Examples.

EXAMPLES 1–4

For operation at atmospheric pressure the reactor consisted of a heated, efficiently stirred vessel with a reflux condenser cooled to −6° C. The initial charge contained:

propionitrile: 77 parts by weight
cupric bromide: 8 parts by weight
lithium bromide: 2 parts by weight and iodine compounds as shown in Table 1 and was maintained at 50° C.

The reactants butadiene: 7 parts by wt. per hr.
hydrogen cyanide: 6 parts by wt, per hr.
oxygen: 8 parts by wt. per hr.

were fed to the reactor. The excess gas can be recovered for recycle.

When steady reaction conditions had been achieved trans-1,4-dicyanobutene-2 was formed at the rate indicated in Table 1, which rates were higher when iodine compounds were present than when they were absent. Moreover, the rates of formation of by-product cyanogen, also indicated in Table 1, were less when iodine compounds were present.

TABLE 1

| Example No. | Additive Iodine Compound | Parts by weight % | Trans-1,4-di-cyanobutene-2 mol/hr/liter | Cyanogen mol/hr/liter | Mole Ratio Cyanogen: Dicyanobutene |
|---|---|---|---|---|---|
| Comparative | Nil | | .0103 | .0110 | 1.06 |
| 1 | Iodine | 0.1 | .0188 | .00288 | .153 |
| 2 | Iodine | 0.5 | .0316 | .00066 | .021 |
| 3 | Sodium Iodide | 0.2 | .0236 | .00296 | .125 |
| 4 | Cuprous Iodide | 4.0 | .0314 | .00072 | .023 |

Rates are expressed per liter of liquid reaction mixture.

EXAMPLE 5

To a solution of 4 parts by weight of cupric bromide, 2 parts; of cuprous iodide and 1 part of lithium bromide in 40 parts of propionitrile held at 50° C in a hot water jacketed tubular reactor at atmospheric pressure was added a vapour phase mixture of hydrogen cyanide (1.15 parts by weight per hour), butadiene (5.8 parts/hour) and oxygen (3.4 parts/hour) via a gas bubbler.

After 78 hours, passage of gas was stopped and the liquid reaction mixture was evaporated to dryness and the residue extracted with toluene from which 15.8 parts of trans-1,4-dicyanobutene-2 crystallised out on cooling to 0° C, a yield of 5.25 moles per mole of copper present in the reaction mixture.

EXAMPLE 6

The mixture propionitrile: 16 parts by weight
cupric bromide: 4 parts by weight
lithium bromide: 1 parts by weight
sodium iodide: 0.5 parts by weight
butadiene: 6.2 parts by weight
hydrogen cyanide: 6.9 parts by weight was charged to a suitable pressure vessel and the pressure adjusted to 4.5 bar absolute with air. After heating and maintaining the temperature at 50° C for 1 hour the reactor was cooled and the excess gas vented. From the product 0.74 parts by weight of trans-1,4-dicyanobutene-2 was obtained equivalent to a rate of 0.174 mole/liter/hour based on the volume of reaction mixture.

EXAMPLE 7

Example 6 was repeated except that pure oxygen was used instead of air. 2.04 parts by weight of trans-1,4-dicyanobutene-2 were obtained equivalent to a production rate of 0.480 mol/liter/hour based on the volume of reaction mixture.

EXAMPLE 8

A mixture consisting of:

propionitrile: 20 ml
cuprous bromide: 2 g
cuprous iodide: 1 g
lithium bromide: 1.5 g
butadiene: 10 ml
hydrogen cyanide: 15 ml
cyanoacetic acid: 1 g
acetone: 1 ml
triphenylphosphine: 0.1 g was stirred in a pressure vessel and charged with oxygen at 4.5 bar absolute then heated at 60° C for 5.5 hr. After releasing pressure the contents were analysed by G.L.C. (gas/liquid chromatography) and found to contain 11.84 g trans-1,4-dicyanobutene-2.

EXAMPLES 9–13

Reaction mixtures containing in each case propionitrile: 20 ml.
cupric bromide: 2 g.
cuprous iodide: 2 g.
lithium bromide: 0.5 g.
oxygen: 4.5 bar absolute and the constituents shown in Table 2. were reacted at the temperatures for the times shown in Table 2. The production of dicyanobutene shown in the Table is up to 6 mols/mol copper for Examples 9 to 11 and approximately 9 mols/mol copper for Examples 12 and 13.

TABLE 2

| Example | | 9 | 10 | 11 | 2 | 13 |
|---|---|---|---|---|---|---|
| Butadiene | ml | 7 | 10 | 10 | 20 | 20 |
| Hydrogen cyanide | ml | 10 | 12 | 12 | 24 | 24 |
| Acetone | ml | | | | 1.0 | |
| Cyanacetic acid | g | 1.0 | | | | |
| Hydrogen bromide aq. | ml | | 1.0 | 1.0 | 1.0 | 1.0 |
| Nitric acid | ml | | 0.1 | 0.1 | 0.1 | 0.1 |
| Temperature | °C | 60 | 50 | 50 | 50 | 50 |
| Time | hr | 17 | 4 | 3 | 22 | 22 |

TABLE 2-continued

| Example | | 9 | 10 | 11 | 2 | 13 |
|---|---|---|---|---|---|---|
| Trans-1,4-dicyanobutene-2 | g | 7.01 | 9.00 | 8.20 | 13.83 | 14.02 |

EXAMPLE 14

A mixture consisting of:

propionitrile: 18 ml
crown ether: 6 ml
cuprous bromide: 2 g
cuprous iodide: 1 g
lithium bromide: 0.5 g
butadiene: 6 ml
hydrogen cyanide: 10 ml was stirred in a pressure vessel and charged with oxygen at 4.5 bar absolute, then heated at 50° C for 4 hours. The product contained 6.8 g. of trans-1,4-dicyanobutene-2.

EXAMPLE 15

This example shows the use of a crude $C_4$ stream from a cracker (containing 41.7% of butadiene)

A mixture consisting of:

propionitrile: 20 ml
cuprous bromide: 2 g
cuprous iodide: 1 g
lithium bromide: 0.5 g
A $C_4$ stream containing 41.7% of butadiene: 10 ml
hydrogen cyanide: 10 ml was stirred in a pressure vessel and charged with oxygen at 4.5 bar absolute then heated at 50° C for 15 hours. The product contained 3.44 g of trans-1,4-dicyanobutene-2.

EXAMPLE 16

The effect of various solvents was examined by charging the following mixture to a pressure vessel equipped with a stirrer.

Solvent: 20 parts by vol.
Cupric bromide: 4 parts by weight.
Lithium bromide: 0.5 parts by weight
sodium iodide: 0.5 parts by weight
Butadiene: 10 parts by volume
Hydrogen cyanide: 10 parts by volume
Oxygen (4.5 bar absolute equiv. to): 0.045 parts by weight The reactor and contents were heated to 50° C and this temperature maintained for 2 hours before cooling and venting excess gas. The residue was dissolved in solvent and the amount of trans-1,4-dicyanobutene-2 in parts by weight was determined by G.L.C. The results are summarised in the Table.

| Solvent | Trans-1,4-dicyano-butene-2 |
|---|---|
| Water | 0.68 |
| Methanol | 0.73 |
| Ethanol | 2.17 |
| isopropanol | 3.20 |
| t-butanol | .95 |
| 2 Phenylethanol | .22 |

-continued

| Solvent | Trans-1,4-dicyano-butene-2 |
|---|---|
| Ethylene glycol | .23 |
| Propane-1,2-diol | .23 |
| m-cresol | 6.52 |
| Tetrahydrofuran | 2.42 |
| Tetrahydropyran | 1.16 |
| Dioxan | .56 |
| 1,2-Dimethoxyethane | 3.91 |
| Diglyme | 2.54 |
| Anisole | .45 |
| Acetic acid | 1.55 |
| Naphthenic acid | .07 |
| Methyl acetate | .97 |
| Diethyl adipate | .41 |
| Acetone | 3.89 |
| Cyclohexanone | .17 |
| Acetophenone | 1.61 |
| Acetylacetone | 3.39 |
| Ethyl cyanoacetate | 1.17 |
| N-Methylformamide | 1.79 |
| Dimethyl formamide | 2.21 |
| N-Methyl-2-pyrrolidone | .43 |
| n-hexane | .17 |
| Toluene | .93 |
| Brombenzene | .52 |
| Dichloromethane | 1.03 |
| Tetrachlorethane | .90 |

EXAMPLE 17

Example 16 was repeated, except that the reaction mixture was heated for 5 hours, using the following compounds as solvent and the quantity of trans-1,4-dicyanobutene-2 indicated (in parts by weight) was obtained.

| Solvent | Trans-1,4-dicyano butene-2 |
|---|---|
| Benzonitrile | 4.11 |
| Adiponitrile | 6.24 |
| Sulpholane | 5.02 |

We claim:

1. A process for the manufacture of dicyanobutene which comprises reacting butadiene with hydrogen cyanide in the molar ratio of about 1:10 to about 10:1 and oxygen or a gas mixture containing oxygen, with the oxygen in molar excess in relation to whichever of the hydrogen cyanide or butadiene is used in the smaller molar amount, in the presence of a catalyst comprising copper ions, ions of at least one halide selected from the group consisting of chloride and bromide, and iodide ions, and of a solvent for the catalyst which solvent does not interfere with the reaction and is not itself extensively changed by the reaction, at a temperature of about 10° to 150° C., the amount of copper ion and of combined said halide ion and iodide ion being from about 0.001 to about 0.2 mole per mole of butadiene, and the proportion of iodide ion in the combined halide and iodide ion being from about 0.1 to about 90% on a molar basis.

2. The process of claim 1 in which the catalyst consists essentially of copper ions, bromide ions and iodide ions.

3. The process of claim 1 in which an alkali metal or alkaline earth metal salt is included in the reaction mixture.

4. The process of claim 3 in which the metal salt is a lithium salt.

5. The process of claim 1 in which the solvent is water or an organic solvent.

6. The process of claim 5 in which the organic solvent is a nitrile.

7. The process of claim 1 in which the butadiene is introduced into the reaction mixture as a crude $C_4$ stream containing butadiene.

8. The process of claim 1 effected by passing butadiene and hydrogen cyanide in vapour form together with oxygen or a mixture containing oxygen through a liquid comprising the catalyst and solvent.

9. The process of claim 1 wherein the molar ratio of hydrogen cyanide to butadiene is in the range of about 1:2 to 4:1.

10. The process of claim 1 wherein the reaction is conducted at a temperature within the range of about 35° C. to about 110° C.

11. The process of claim 1 wherein the proportion of iodide ion in the combined halide and iodide ion is present between about 1% to about 10% on a molar basis.

* * * * *